(12) United States Patent
Marin (10) Patent No.: US 9,924,968 B2
(45) Date of Patent: Mar. 27, 2018

(54) EXTERNAL FIXATOR ASSEMBLY

(71) Applicant: Luis E. Marin, Hialeah, FL (US)

(72) Inventor: Luis E. Marin, Hialeah, FL (US)

(73) Assignee: MDPO LLC, Sunrise, FL (US)

(*) Notice: Subject to any disclaimer, the term of this patent is extended or adjusted under 35 U.S.C. 154(b) by 0 days.

(21) Appl. No.: 14/513,749

(22) Filed: Oct. 14, 2014

(65) Prior Publication Data

US 2015/0032107 A1    Jan. 29, 2015

Related U.S. Application Data (63) Continuation-in-part of application No. 12/319,823, filed on Jan. 13, 2009, now abandoned.

(51) Int. Cl.
*A61B 17/00* (2006.01)
*A61B 17/64* (2006.01)
*A61B 17/62* (2006.01)

(52) U.S. Cl.
CPC .......... *A61B 17/6425* (2013.01); *A61B 17/62* (2013.01)

(58) Field of Classification Search
CPC ...... A61B 17/60–17/666; A61B 17/80–17/826
See application file for complete search history.

(56) References Cited

U.S. PATENT DOCUMENTS

| | | |
|---|---|---|
| 2,020,262 A | 11/1935 | Longfellow |
| 2,035,952 A | 3/1936 | Ettinger |
| 2,079,567 A | 5/1937 | Anderson |
| 2,393,831 A | 1/1946 | Stader |

(Continued)

FOREIGN PATENT DOCUMENTS

| | | |
|---|---|---|
| RU | 2391931 C1 | 6/2010 |
| SU | 1769871 A1 | 10/1992 |

(Continued)

OTHER PUBLICATIONS

Schwartsman V et al: "Techniques of Fracture Reduction: The Ilizarov Method", Techniques in Orthopaedics, Gaithersburg, MD, US, vol. 5, No. 4, Dec. 1, 1990 (Dec. 1, 1990), pp. 53-59, XP000667194, *p. 58, right-hand column, lines 4-10: figure 8*.

*Primary Examiner* — Jan Christopher Merene
*Assistant Examiner* — Steven Cotroneo
(74) *Attorney, Agent, or Firm* — Malloy & Malloy, P.L.

(57) ABSTRACT

A support structure for use with an external fixator assembly including, but not limited to, a fixator assembly for the ankle area of the body which may further include an ankle stabilization portion. The support structure is similar in function but distinguishable in structure from a "halo-ring" and comprises a base having a substantially annular configuration and being operatively disposed in at least partially surrounding relation to a leg area corresponding to the stabilized ankle area. An extension structure includes at least one but preferably a plurality of two elongated extension members extending outwardly from the base and in spaced relation to and substantially aligned with the ankle stabilization portion. The base and the two extension members are structured for connection to a plurality of struts which may be variably and selectively disposed in interconnecting relation to the ankle stabilization area and/or other portions of the external fixator assembly.

12 Claims, 5 Drawing Sheets

(56) References Cited

U.S. PATENT DOCUMENTS

| | | | |
|---|---|---|---|
| 2,406,987 A | 9/1946 | Anderson | |
| 3,941,123 A | 3/1976 | Volkov et al. | |
| 4,176,627 A | 12/1979 | Bassi | |
| 4,308,863 A | 1/1982 | Fischer | |
| 4,338,927 A * | 7/1982 | Volkov et al. | 606/56 |
| 4,535,763 A | 8/1985 | Jaquet | |
| 4,607,625 A | 8/1986 | Schenck | |
| 4,624,249 A | 11/1986 | Alvarez Cambras | |
| 4,696,293 A | 9/1987 | Ciullo | |
| 4,768,524 A | 9/1988 | Hardy | |
| 5,062,844 A | 11/1991 | Jamison et al. | |
| 5,067,954 A | 11/1991 | Ilizarov | |
| 5,087,258 A | 2/1992 | Schewior | |
| 5,139,498 A * | 8/1992 | Astudillo Ley | A61B 17/8076 606/216 |
| 5,358,504 A | 10/1994 | Paley et al. | |
| 5,468,242 A * | 11/1995 | Reisberg | A61B 17/8085 606/151 |
| 5,496,319 A | 3/1996 | Allard et al. | |
| 5,540,686 A * | 7/1996 | Zippel et al. | 606/56 |
| 5,578,041 A | 11/1996 | Nash et al. | |
| 5,681,309 A * | 10/1997 | Ross et al. | 606/56 |
| 5,702,389 A | 12/1997 | Taylor et al. | |
| 5,743,898 A | 4/1998 | Bailey et al. | |
| 5,776,132 A * | 7/1998 | Blyakher | 606/56 |
| 5,788,695 A | 8/1998 | Richardson | |
| 5,814,048 A * | 9/1998 | Morgan | A61B 17/8085 606/283 |
| 5,891,143 A * | 4/1999 | Taylor et al. | 606/56 |
| 5,931,837 A | 8/1999 | Marsh et al. | |
| 6,030,386 A * | 2/2000 | Taylor et al. | 606/56 |
| 6,328,737 B1 | 12/2001 | Moorcroft et al. | |
| 6,355,037 B1 * | 3/2002 | Crosslin et al. | 606/57 |
| 6,461,358 B1 | 10/2002 | Faccioli et al. | |
| 6,964,663 B2 * | 11/2005 | Grant et al. | 606/54 |
| 7,025,790 B2 | 4/2006 | Parks et al. | |
| 7,048,735 B2 | 5/2006 | Ferrante et al. | |
| 7,189,237 B2 | 3/2007 | Huebner | |
| 7,361,176 B2 | 4/2008 | Cooper et al. | |
| 7,422,593 B2 * | 9/2008 | Cresina et al. | 606/54 |
| 7,806,843 B2 | 10/2010 | Marin | |
| 7,887,498 B2 | 2/2011 | Marin | |
| 8,251,937 B2 | 8/2012 | Marin | |
| 8,439,914 B2 | 5/2013 | Ross et al. | |
| 2002/0010465 A1 * | 1/2002 | Koo et al. | 606/57 |
| 2004/0138659 A1 | 7/2004 | Austin et al. | |
| 2004/0167530 A1 | 8/2004 | Hamel | |
| 2005/0149018 A1 * | 7/2005 | Cooper | A61B 17/6425 606/54 |
| 2005/0251135 A1 | 11/2005 | Riccione et al. | |
| 2007/0055234 A1 * | 3/2007 | McGrath et al. | 606/56 |
| 2007/0161984 A1 | 7/2007 | Cresina et al. | |
| 2007/0255280 A1 | 11/2007 | Austin et al. | |
| 2009/0082709 A1 | 3/2009 | Marin | |
| 2009/0105621 A1 * | 4/2009 | Boyd | A61F 5/0195 602/3 |
| 2009/0177197 A1 | 7/2009 | Marin | |
| 2009/0275944 A1 | 11/2009 | Huebner et al. | |
| 2010/0179548 A1 | 7/2010 | Marin | |
| 2010/0234844 A1 | 9/2010 | Edelhauser et al. | |
| 2010/0234896 A1 * | 9/2010 | Lorenz | A61B 17/74 606/286 |
| 2012/0209163 A1 | 8/2012 | Phillips | |
| 2014/0257287 A1 | 9/2014 | Chang et al. | |
| 2014/0276260 A1 | 9/2014 | Marin | |

FOREIGN PATENT DOCUMENTS

| | | |
|---|---|---|
| WO | WO 2007/067297 | 6/2007 |
| WO | WO2007111576 A2 | 10/2007 |
| WO | WO 2009/042167 | 4/2009 |
| WO | WO 2010/083033 | 7/2010 |
| WO | WO 2014/152559 | 9/2014 |
| WO | 2016196498 A1 | 12/2016 |

* cited by examiner

EXTERNAL FIXATOR ASSEMBLY

CLAIM OF PRIORITY

The present application is a continuation-in-part application of previously filed, now pending application having Ser. No. 12/319,823, filed on Jan. 13, 2009 incorporated herein by reference.

BACKGROUND OF THE INVENTION

Field of Invention

This invention is directed to a support structure similar in function but distinguishable in structure to a halo-type support ring adapted for use as an operative component of an external fixation assembly for an ankle or other area of the patient's body. The support structure includes an annular base dimensioned and configured for disposition in surrounding relation to a leg area associated with the ankle being stabilized. An extension structure comprising a plurality of extension members is connected to the base, wherein the base and extension members are structured for connection to one or more strut members disposed in interconnecting relation to and between the support structure and the other components of the external fixator assembly.

Description of the Related Art

In the medical treatment of pathologies including, but not limited to, injuries, fractures, etc. to the bone and joints, external fixator assemblies are commonly used to maintain segments of the bone in an intended and/or required stabilized orientation. By way of example, fixator assemblies of the type described may be utilized to treat the fusion of bone tissue as well soft tissue injuries, and situations involving a union of bones which otherwise are difficult to heal. As such, known or conventional fixator assemblies vary in structure, dimension and configuration and are correspondingly adapted to be used with various portions of the body to which they are attached.

Typical fixator structures include one or more connecting bars or rods as well a plurality of clamps for adjustably securing fixation pins, wires, etc. to the bone portions being affected. Further, transfixion pins or wires of the types commonly utilized may extend completely through the bony tissue or may be anchored therein, such as when the long bones of the leg are involved directly or indirectly with the treatment or healing procedure. Further, the term "transfixion member" is generally recognized in the medical field as including the describing of elongated pins which extend completely or at least partially through the bony tissue involved. In contrast, smaller, thicker "half pins" may be utilized in substantially the same manner to stabilize affected tissue but being of a length insufficient to extend completely through the affected bone, joint, etc. This term may also be used in a more generic sense in referring to stabilizing devices, other than pins, such as wires, reduction wires, screws, clamps, etc.

In addition, known external fixator assemblies of the type described may also include support rings which encircle a corresponding body member, wherein such rings or like support members serve as a supportive base to facilitate proper location of the aforementioned transfixion members. Accordingly, it is commonly understood in the medical profession that fixator assemblies are used to maintain proper orientation of one or more bones or bone segments relative to one another to facilitate healing or alignment.

However, the proper stabilization of tissue typically associated with the joint areas of a patient's body such as, but not limited to, the ankle joint as well as the wrist and other smaller bones associated with the hand involves additional considerations. In particular when dealing with the ankle area and the associated tissue serving to interconnect the foot to the lower portion of the leg, the fixator clamps or fixation clamps support blocks are frequently connected to an encircling halo-ring or like support member. These devices are mounted on the ring or other support member to properly position a transfixion pin or like member at a proper height or corresponding distance above the supporting ring in order to engage and thereby properly orient the affected bones of the ankle joint to the foot. In utilizing these support blocks, transfixion clamps, etc., one commonly recognized problem or disadvantage associated therewith is the possibility these devices obscuring important or necessary portions of the ankle joint when X-rayed. In addition, the proper placement of one or more of such clamps, support blocks, etc. is time consuming for medical personnel and may lack a certain versatility and/or accuracy associated with the accurate placement of a transfixion pin or like transfixion member in the fixed orientation or otherwise support of the various bones of the ankle joint.

Accordingly there is a need in the medical profession for a support structure which is at least minimally similar in function, but clearly distinguishable in structure, from a known halo-type ring support structures. Such an improved support structure allows greater versatility in the positioning of interconnecting struts serving to interconnect and support various components of an external fixator assembly in their intended operative position. Further, the dimension, configuration and overall structure of such a proposed support structure is such as to be usable with an external fixator assembly of the type used to stabilize the ankle area of the patient. As such, the support may be disposed in interconnected, spaced relation to an ankle stabilization portion of the external fixator assembly and in surrounding relation to an adjacent leg area associated with the ankle being stabilized. The proposed support structure of the present invention is structured to facilitate the support and connection of a plurality of interconnecting struts. Further, the support structure is also structured to have mounted thereon and/or connected thereto a plurality of transfixion members which extend radially inward from the proposed support structure into engaging relation to the relatively long bones of the corresponding leg area.

Accordingly there is a need in the medical profession for an a support structure component useable as part of an external fixator assembly which more efficiently stabilizes the hard tissue associated with the foot and ankle areas and/or the associated bones of the lower leg.

SUMMARY OF THE INVENTION

The present invention is directed to a support structure for use with or as part of an external fixator assembly of the type specifically, but not exclusively, intended for the stabilization of an ankle area of the body. As such, the various embodiments of the support structure of the present invention are operatively disposed to function somewhat similarly to the known halo-type support ring, as generally set forth above. However, the structural features of the support ring structure of the present invention are clearly distinguishable from known or conventional halo-type rings, as set forth in greater detail hereinafter.

As referred to herein, the term "ankle area" refers to and is intended to describe the ankle joint, as well as bones and associated tissue of the foot and lower portions of the leg bones including the fibula and tibia. Further, in properly describing the intended position and orientation of the various preferred embodiments of the support structure of the present invention and the remainder of the external fixator assembly associated therewith, terminology including "length of the ankle area" and/or "height of the ankle area" may be utilized synonymously. These terms are meant to refer to the general distance between the bottom of the foot and an area of the lower part of the leg above the ankle joint. Further the ankle area, as used herein, is meant to be descriptive of the bones and other tissue associated with the foot, ankle joint and lower leg which serve to facilitate the functioning of the ankle joint and intended, relative movements of the corresponding foot and leg connected to the ankle joint.

Accordingly, the support structure of the present is used independently of or in combination with an external fixator assembly which may further comprise an ankle stabilization portion. The ankle stabilization portion is disposed adjacent the ankle area and foot and is structured to support at least one transfixion pin or like transfixion member in operative engagement with the bones or other associated tissue associated with the ankle area. Moreover, the support structure of the present invention comprises a base preferably having a continuous, annular configuration or be otherwise configured and dimensioned to at least partially, but in most applications completely surround the leg area of a patient's body which is substantially adjacent to the ankle area being stabilized.

Further, the support structure of the present invention includes an extension structure comprising at least one but more practically a plurality of extension members or arms extending outwardly from the base. Each of the arms is elongated to a sufficient degree that, when combined with the corresponding dimensions of the base, extend along at least a portion and/or a majority of the length of corresponding, spaced apart portions of the ankle stabilization portion of the external fixator assembly. In addition, a plurality of apertures or through holes are disposed about the continuous length of the base and also along the length of the extension members. These apertures will serve as connecting sites for at least one, but more practically, a plurality of elongated studs. As described herein, the one or more studs serve to interconnect the support structure of the present invention with the ankle stabilization portion as well as any additional conventional halo-type rings and/or additional support structures.

Therefore, the interconnecting struts serve to place both the ankle stabilization portion and/or other, conventional halo-type rings in spaced relation to the support structure as these various components extend along the length of the ankle area or leg upwardly from the position of the ankle stabilization portion adjacent the ankle area being stabilized. Further, the plurality of apertures or through holes defining the connecting sites for the struts are disposed such that the plurality of struts may be disposed at a variety of different locations in order to provide greater versatility to the medical personnel when placing the struts and the various components of the external fixator assembly in order to eliminate the possibility of interference with X-rays views, which are typically required.

Other features associated with the support structure of the present invention include the plurality of preferably two extension members extending outwardly from the base in a common direction and in spaced relation to one another. In at least one preferred embodiment, the two extension members or arms may also be disposed in parallel relation to one another and may be further disposed in substantially coplanar relation to one another and/or to the base. In order to provide sufficient structural integrity to the two extension members, at least one embodiment of the support structure includes a brace structure. The brace structure preferably comprises at least two brace segments each disposed in interconnecting, reinforcing relation between an exterior periphery of the base and a corresponding peripheral edge or other appropriate portion of a different one of the extension members or arms.

As represented hereinafter in greater detail, the external fixator assembly, including the support structure of the present invention, is structured to connect one or more transfixion pins or like transfixion members so as to extend transversely inward and into stabilizing engagement with the leg bone(s) or other tissue associated with the ankle area at various points along the height or length of the leg and/or ankle area. Further, each of the one or more transfixion pins can be connected to a plurality of different locations along the length thereof. Therefore the disposition of the base and extension structure of the support structure as well as the structure of at least some of the remainder of the external fixation assembly provides significant versatility in positioning each of the one or more transfixion pins or members at any one of a plurality of different locations relative to the leg and associated ankle area being stabilized.

Therefore, the positioning of the transfixion pin(s) or member(s) into stabilizing engagement with intended tissue of the leg and ankle area, in the manner described herein, eliminates or significantly reduces the need for conventional support blocks or clamps to connect the transfixion pin(s). As set forth above, the use of such known devices and procedures for orienting of the transfixion pins relative to a predetermined body part is time consuming and has a tendency to obscure X-rays or other viewing facilities of the body part. Therefore the use of the various preferred embodiments of the present invention eliminate or significantly reduce such known and well recognized disadvantages.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

DETAILED DESCRIPTION OF THE PREFERRED EMBODIMENT

Like reference numerals refer to like parts throughout the several views of the drawings.

Figure 2:
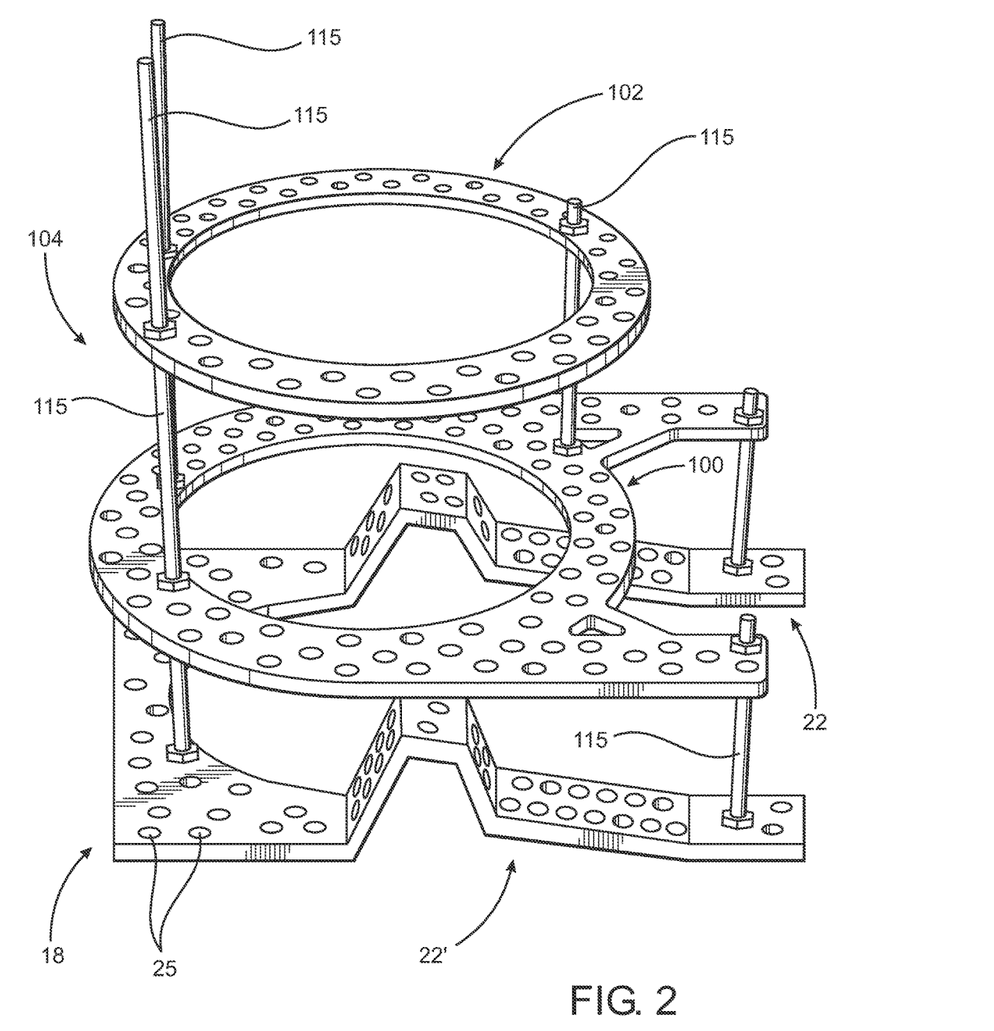
FIG. 2 is a perspective view of the support structure of the present invention as represented in the embodiment of FIG. 1 incorporated within and at least partially defining an external fixator assembly of the type adapted for use in the stabilization of an ankle area.
Figure 3:
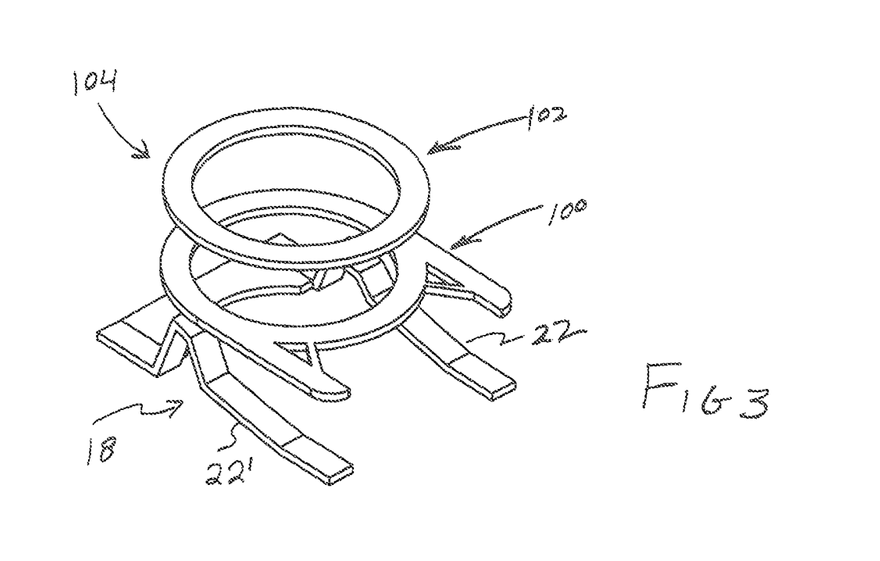
FIG. 3 is a perspective view of the embodiment of FIG. 2 in at least partially schematic form.
Figure 4:
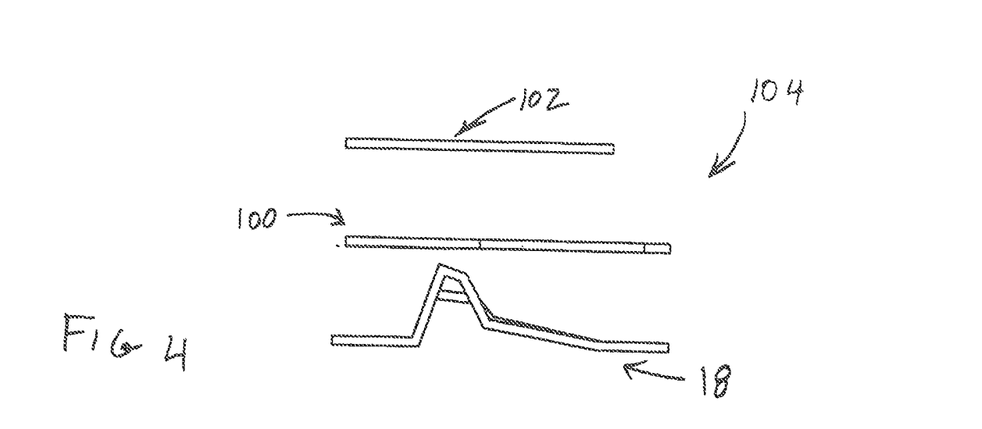
FIG. 4 is a side view of the embodiment of FIG. 3.

As represented in the accompanying Figures, the support structure of the present invention is generally indicated as 100 and is structurally distinguishable from the conventional halo support ring generally indicated as 102 in the embodiments of FIGS. 2-4. Moreover, each of a plurality of preferred embodiments of the support structure 100 of the present invention is adaptable for use in combination with an external fixation assembly generally indicated as 104 in the embodiments of FIGS. 2-4. Further, as will also be discussed in greater detail hereinafter, the external fixator assembly 104 is structured to be operatively positioned and used in a location substantially adjacent to an ankle area generally indicated as 12 in FIG. 5 of a patient. As set forth above, the ankle area 12 is meant to be descriptive of substantially the entire area represented in FIG. 5, which includes the ankle joint, foot, corresponding portions of the leg bones, including the fibula and tibia, as well as the associated components and tissue. In addition, the terms "height" and "length" of the ankle area 12 are used synonymously herein and refer to the distance from substantially the bottom of the foot, as at 14, to at least a portion the long bones of the leg, as at 16, 16'.

Figure 1:
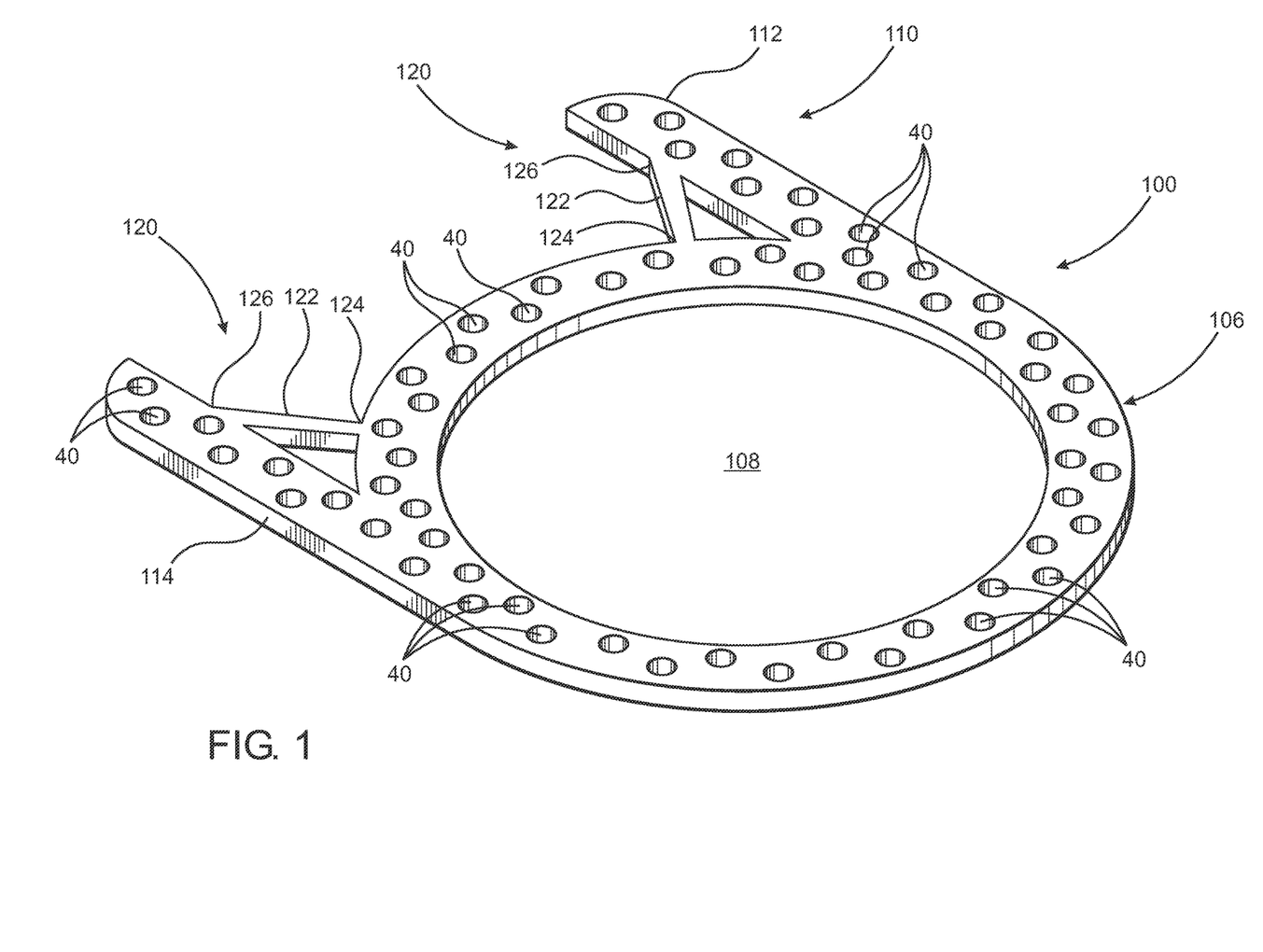
FIG. 1 is a perspective view of a support structure of the present invention.
Figure 5:
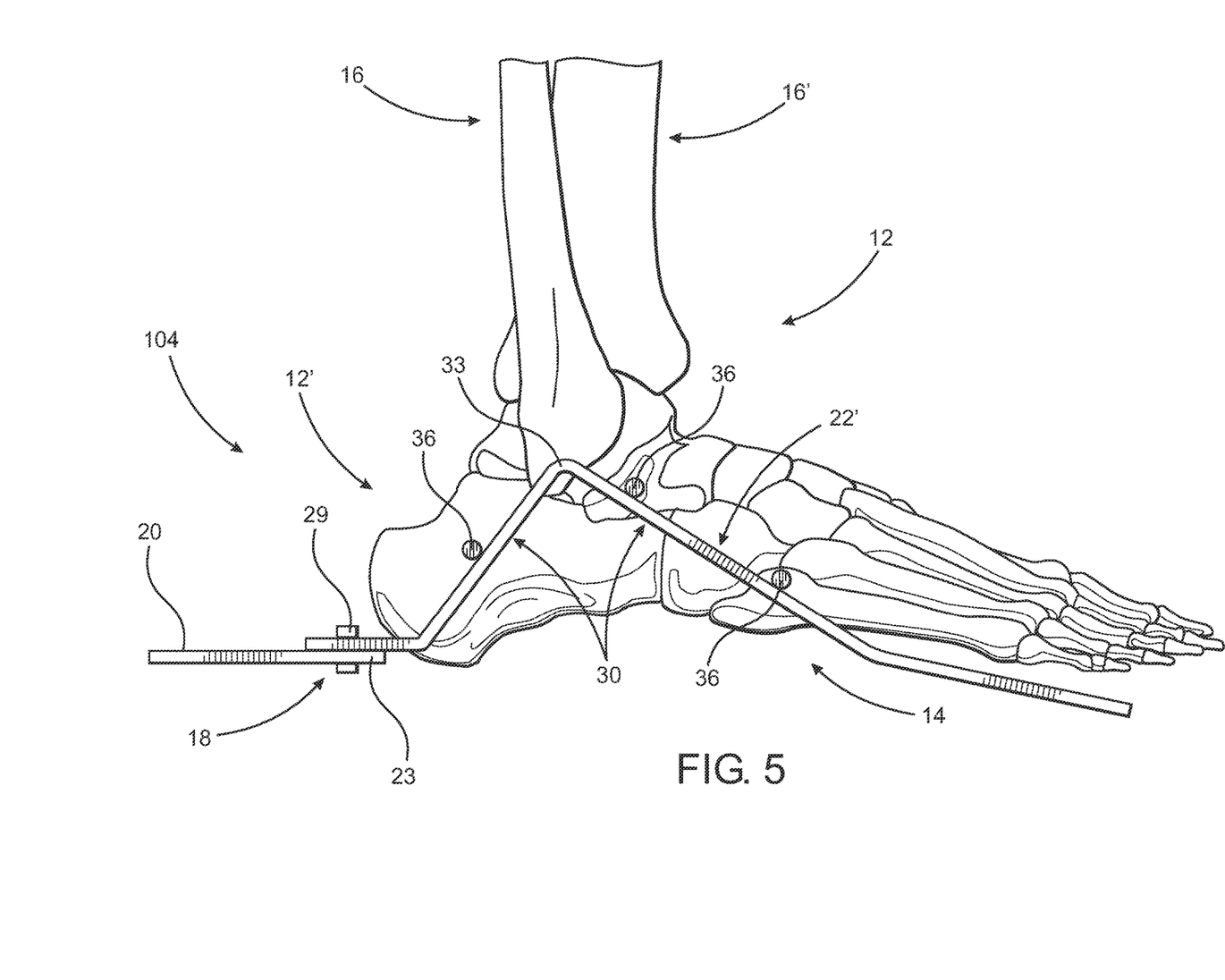
FIG. 5 is a side view in partial cutaway and schematic form of an external fixator assembly modified from that of FIGS. 2 and 3 operatively positioned relative to an ankle area of a patient.

Therefore, with primary reference to FIG. 1, the support structure 100 of the present invention includes a base generally indicated as 106 preferably having an annular configuration and an open interior 108. The open interior 108, as well as the circumferential dimension of the base 106, are sufficient to dispose the base 106 in substantially surrounding relation to the leg portion associated with the leg bones 16, 16' adjacent the ankle portion 12 being stabilized, as schematically represented in FIG. 5. In addition the support structure 100 also includes an extension structure generally indicated as 110 comprising at least one but preferably a plurality of two extension members or extension legs 112 and 114. Each of the extension members 112 and 114 includes an elongated straight line or rectilinear configuration and is integrally connected to and extends outwardly from a different, opposite end or side of the base 106 preferably in a substantially common direction and from a common end. Therefore, as represented throughout the figures, the extension structure 110 including the extension legs 112 and 114 form an integral, one-piece construction with the base 106. As such, the common directional orientation of the extension members 112 and 114 serves to dispose these members in spaced relation to one another. Moreover, in at least one embodiment the extension members 112 and 114 may be disposed in substantially parallel relation and coplanar relation to one another along the respective lengths thereof.

Figure 6:
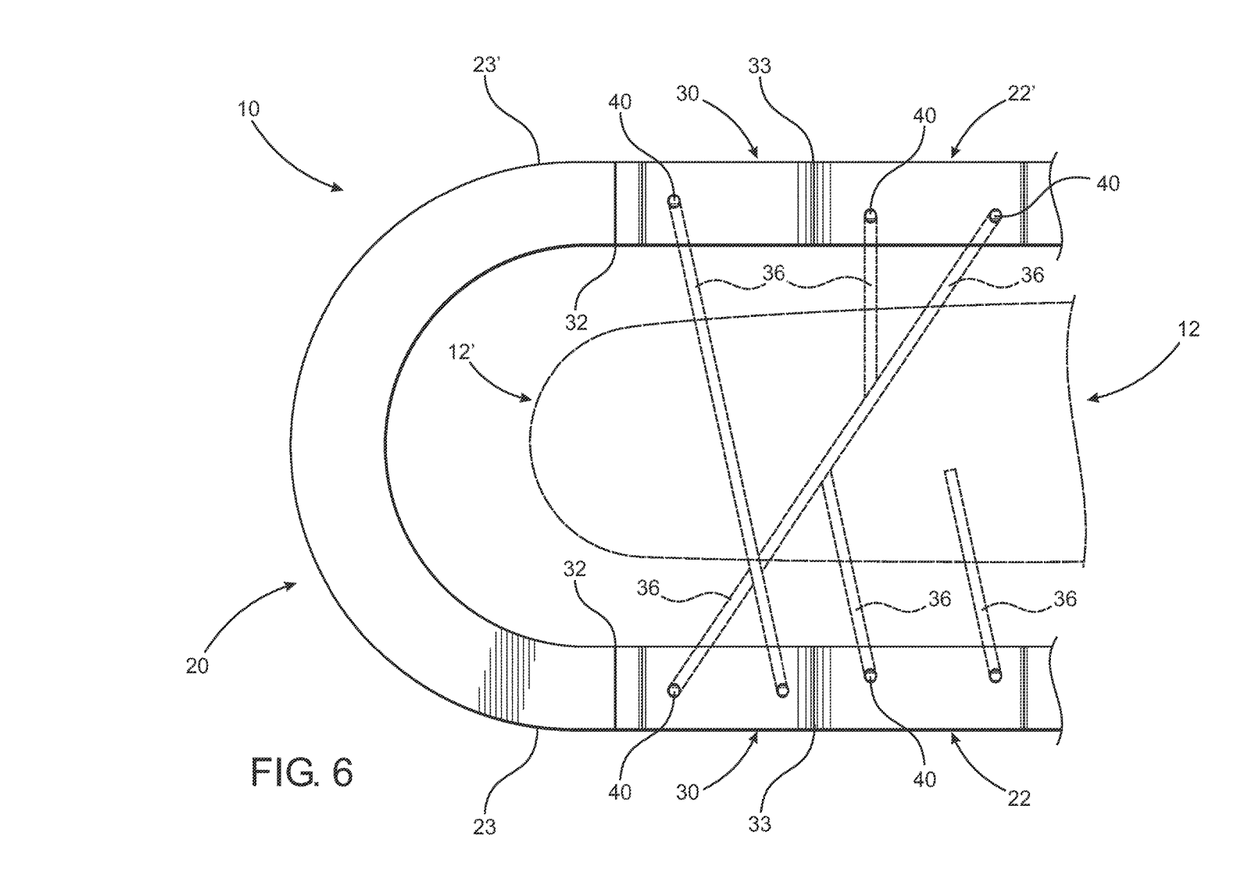
FIG. 6 is a top view in partial cutaway and schematic form of the fixator assembly of FIG. 5 operatively positioned relative to the foot or lower leg portion of an ankle area of a patient.

Further, the structure of the extension structure 110 may be defined by the extension members 112 and 114 being disposed in substantially coplanar relation to the base 106 and/or in coplanar relation to one another and to the base 106, along the entire, respective lengths of the extension members 112 and 114 and the base 106. Additional structural features of the support structure 100, including both the base 106 and each of the plurality of preferably two extension members or arms 112 and 114 including a plurality of apertures or open, through holes 40. The apertures 40 define a plurality of connection sites and structures which facilitate the attachment and/or mounting of a plurality of supporting studs 115 in a variety of operative positions relative to the support structure 100 and the remaining components of the external fixation assembly 104, including the ankle stabilization portion 18 and the substantially conventional halo-support ring 102. Further, the plurality of apertures 40 defining the aforementioned connection sites are also adaptable to facilitate connection, mounting and support of a plurality of transfixion members 36, as represented in FIGS. 5 and 6. As such, when applied or mounted on the support structure 100, including the base 106 and the extension members 112 and 114, the transfixion members 36 may extend radially inward into an engagement with the leg bone 16, 16', surrounded by the base 106. As such, the support structure 100 will serve to support, securely position and thereby stabilize the external fixator assembly 104, as well as the various components thereof, including the ankle stabilization portion 18 and the conventional halo-type support ring 102.

Other structural features of the support structure 100 include the provision of a brace structure generally indicated as 120. The brace structure 120 includes a plurality of brace segments 122 equal in number to that of the plurality of preferably two extension members 112 and 114. As such, the brace segments 122 are disposed in interconnecting, supporting and reinforcing relation between the exterior periphery of the base 106, as at 124, and a corresponding inner peripheral side or edge 126 of different ones of the extension members 112 and 114. As represented in at least FIGS. 1 and 2, each of the brace segments 122 include a straight line or rectilinear configuration and may be integrally connected to the base 106 and the corresponding extension member 112 and 114 when in their respective reinforcing positions. As such, the base 106, the extension structure 110, including the extension members 112 and 114 along with the brace segments 122 collectively form and/or are structured to define a one-piece construction. As further represented in at least FIG. 1, each of the brace segments 122 are disposed at an angular relation to the length of the corresponding extension members 112 and 114 as they interconnect the base 106 and correspondingly disposed ones of the extension members 112 and 114.

For purposes of clarity the various operative and/or structural components of one type of external fixator assembly are represented in appropriate detail in FIGS. 5 and 6. Accordingly, the external fixator assembly 104 may comprise an ankle stabilization portion 18 and possibly a conventional halo-type support ring 102. As will be apparent in the description of the fixator assembly 104 hereinafter provided, the ankle stabilization portion 18 may include one or more contoured segments 22 and 22' operatively positioned relative to the ankle area 12. Further, the one or more contoured segments utilized may be selected from a larger plurality of contoured segments 22, 22', etc., which may differ from one another at least in dimension and configuration, as represented in the structural modifications of the external fixator assembly 18 represented in FIGS. 2 through 4. With primary reference to FIG. 5, the base segment 20, defining at least a portion of the ankle stabilization portion 18, preferably includes a curvilinear configuration which may be more specifically defined by an arcuate or semicircular shape. As such, the base segment 20 terminates in oppositely disposed free ends 23 and 23'. Further, a plurality of apertures, through holes or other appropriate structure 25 are positioned substantially along the length of the base segment 20 and are provided to facilitate the connection of one or more struts 115 to the base segment 20 preferably using fixation bolts, which are not shown for purposes of clarity. Such struts 115 and interconnecting fixation bolts are well-known in the medical profession and are used to support and/or dispose the ankle stabilization portion 18 in a stabilized position relative to the ankle area 12. As set forth above and represented in the various Figures, the struts 115 serve to interconnect the components of the external fixator assembly 104, including the conventional halo-type ring 102 and the support structure 100 located above the ankle area 12, along the length of the leg and in surrounding relation to the bones 16 and 16'.

Accordingly, as represented in FIGS. 5 and 6, the base segment 20 is disposed in at least partially surrounding, spaced relation to a portion of the ankle area 12, such as in the vicinity of the heel 12'. For purposes of clarity, the plurality of apertures, through holes or like connecting facilities 25 are not pictured in FIG. 5 but are in FIG. 2 and are intended to be present therein during the actual practical application or use of the fixator assembly 104. With further reference to both FIGS. 5 and 6, operative placement and use of the fixator assembly 104 comprises the supported disposition of at least one contoured segment 22 or 22' adjacent to an appropriate side of the ankle area 12. More specifically, contoured segment 22', having the smaller or lesser protruding contoured portion 30 is normally placed adjacent the lateral side of the foot and/or ankle area 12. In cooperation therewith, the contoured segment 22, having the larger or greater outwardly protruding portion 30 is normally, but not exclusively, appropriately positioned adjacent the medial side of the foot and/or ankle area 12.

As represented in FIG. 5, operative disposition and use of the fixator assembly 10 may comprise utilization of two of the contoured segments 22 and 22', wherein each is connected to correspondingly disposed ends 23 and 23' of the base segment 20. It is noted that the interconnection of the one or more contoured segments 22 and 22' to the base segment 20 may be removably connected, in a stable manner, through the use of appropriate connectors as at 29.

It is emphasized that common structural features do exist between each of a plurality of contoured segments 22, 22', etc. However, each of a possible larger number of contoured segments 22, 22', etc. may vary in dimension and configuration to accommodate accurate placement of a plurality of transfixion wires or members 36 relative to different portions of the ankle area 12.

Accordingly, each of the contoured segments 22, 22', etc. includes a contoured portion generally indicated as 30 disposed in spaced relation to at least one end 32 thereof, but more practically in spaced relation to opposite ends 32 and 32' thereof. As such, the contoured segment 30, in at least one preferred embodiment of the fixator assembly 10, is disposed intermediate the opposite ends 32 and 32'. Also, one of these opposite ends, such as at 32, is fixedly or removably connected to a correspondingly disposed end 23 of the base segment 20. Further, each of the contoured segments 22, 22', etc. comprise the contoured portion 30 having a substantially angular configuration as it protrudes transversely outward from a remainder of the length of the corresponding contoured segment 22, 22', etc. Moreover, each of the contoured portions 30 terminates at what may be generally referred to as an apex or upper portion of the contoured segment 30, as at 32. Therefore, when one or more of the contoured segments 22, 22', etc. are operatively positioned, a contoured portion 30 of each of the one or more contoured segments 22, 22', etc. extends transversely outward from a remainder of the corresponding contoured segment 22 or 22' along the height or length of the ankle area 12 as best demonstrated in FIG. 5. Accordingly, each of the contoured segments 22, 22', etc. are structured to be connected to and support one or more of a plurality of transfixion members or transfixion wires 36, as represented in FIGS. 5 and 6. As such, each of the one or more transfixion wires or pins 36 extend transversely inward, toward the appropriate portion of the ankle area 12, from any one of a plurality of possible locations on the contoured segment 22, 22', etc. including, but not limited to, being connected to the contoured portion 30 or other portions of the length of the corresponding contoured segment.

As such, the contoured portions 30 of each of the contoured segments 22 and 22' will be located adjacent and in operative relation to an at least minimally different portion of the various bones or other tissue of the ankle area 12. This in turn will facilitate and enhance the versatility of accurately and efficiently placing one or more transfixion wires, pins or like members 36 into engaging, stabilizing relation to the intended bones or other tissue of the ankle area 12. More specifically, as each of the contoured portions 30 of each contoured segment 22, 22', etc. extend transversely outward from the remainder of the length of the corresponding contoured segments 22, 22', etc., the transversely inward ability to position one or more of the transfixion members 36 into engaging relation with appropriate tissue of the ankle area 12.

Additional structural details of each of the plurality of contoured segments 22, 22', etc. include the provision of a plurality of apertures or through holes 40, or other appropriately structured connecting sites, along the length of the contoured portion 30 as well as the remainder of the length of the corresponding contoured segment 22, 22' etc. These apertures 40 facilitate the interconnection of the one or more transfixion members 36 thereto, such that the one or more transfixion members 36 may be located at any one of a plurality of locations along the contoured portion 30 as well as the remainder of the length of the contoured segment 22, 22', etc. This further adds in the versatility and accurate placement of the transfixion member 36 along the entire length of the corresponding contoured segments 22, 22', etc. Also, when each of the contoured segments 22, 22', etc. are fixedly but removably connected to the appropriate ends as at 23 and 23' of the base segment 20, additional apertures or other appropriate structures may be provided to facilitate placement of an appropriate connector 29, as represented in FIG. 5. It is further emphasized that when two contoured segments are used, as in the embodiment of FIG. 5, they may comprise different or substantially equivalent dimensions and configurations, dependent on the medical requirements in the stabilization or other treatment of the ankle area 12.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A support structure for use with an external fixator assembly, said support structure comprising:
    a base having a continuous, closed, annular configuration and an open interior,
        said open interior dimensioned to receive a leg of an individual there through concurrent to operative placement of said base in surrounding relation to the leg of the individual, an extension structure fixedly connected to opposite sides of said base and extending outwardly from a common end thereof, said extension structure comprising two rectilinear, elongated extension members each integrally connected in a fixed position to a different one of said opposite sides of said base and extending outwardly therefrom in a same direction and in parallel, equally spaced relation to one another along the lengths thereof, a brace structure integrally interconnecting said base and said two extension members in fixed relation to one another and disposed in a fixed position between an outer periphery of said base and an inner periphery of the each of said two extension members, said two extension members, said base and said brace structure disposed in coplanar relation to one another and collectively defining an integral, one-piece construction, and each of said two extension members and said base structured for supported attachment, along and through the respective lengths thereof, of at least one strut associated with the external fixator assembly.

2. The support structure as recited in claim 1 wherein said brace structure comprises two brace segments; each of said two brace segments integrally interconnecting a different correspondingly disposed one of said two extension members in fixed relation to said base and connected in a fixed position relative to said base and said different correspondingly disposed ones of said two extension members.

3. The support structure as recited in claim 1 wherein each of said brace segments is integrally interconnected in a fixed position between said outer periphery of said base and an inner peripheral edge of the correspondingly disposed one of said two extension members.

4. The support structure as recited in claim 3 wherein each of said brace segments is disposed at an angular orientation relative to the length of the correspondingly disposed one of said two extension members.

5. The support structure as recited in claim 1 wherein said base and said two extension members include a plurality of through holes disposed along respective lengths thereof, said plurality of through holes collectively structured for receipt and a supported attachment of a plurality of the struts thereto.

6. The support structure as recited in claim 1 wherein each of said two extension members and corresponding, substantially aligned side portions of said base collectively comprise a length substantially equivalent to at least a majority of a length of corresponding side portions of an ankle stabilizing portion of the external fixator assembly, when disposed into an operative disposition in spaced relation above the ankle stabilizing portion.

7. A support structure for use with an external fixator assembly, said support structure comprising:

a base having a continuous, closed annular configuration and an open interior, said open interior dimensioned to receive a leg of an individual there through concurrent to operative placement of said base in surrounding relation to the leg of the individual, an extension structure comprising at least two rectilinear elongated extension members each integrally connected in a fixed position to a different, opposite side of said base, each of said extension members terminating in a free end and extend outwardly from said base in equally spaced relation to one another along the lengths thereof and in spaced, parallel relation to one another and in a same direction, a brace structure comprising two brace segments; each of said two brace segments interconnected in a fixed position between an outer periphery of said base and a different correspondingly disposed one of said extension members, each of said two brace segments integrally interconnecting said correspondingly disposed ones of said extension members in fixed relation to said base, said base, said two extension members and said two brace segments all fixedly disposed in coplanar relation to one another and collectively defining an integral one-piece construction, and each of said extension members and said base structured for supported attachment along respective lengths thereof, of at least one strut associated with the external fixator assembly.

8. The support structure as recited in claim 7 wherein each of said two brace segments is integrally connected in spaced relation to one another, each of said two brace segments including an outer end integrally connected in a fixed position to an inner peripheral edge of said different correspondingly disposed one of said extension members.

9. The support structure as recited in claim 7 wherein each of said two brace segments includes an inner end connected to said outer periphery of said base and an outer end integrally connected in a fixed position to an inner peripheral edge of said correspondingly disposed one of said extension members.

10. The support structure as recited in claim 9 wherein each of said brace segments is disposed at an angular orientation relative to the length of said correspondingly disposed one of said extension members, to which it is attached.

11. The support structure as recited in claim 7 wherein said base and said extension members include a plurality of through holes disposed along respective lengths thereof, said plurality of through holes collectively structured for receipt and supported attachment of a plurality of the struts thereto.

12. The support structure as recited in claim 7 wherein each of said two extension members and corresponding, substantially aligned side portions of said base collectively comprise a length substantially equivalent to at least a majority of a length of corresponding side portions of an ankle stabilizing portion of the external fixator assembly, when disposed into an operative disposition in spaced relation above the ankle stabilizing portion.

\* \* \* \* \*